(12) United States Patent
Burnell et al.

(10) Patent No.: US 6,500,632 B1
(45) Date of Patent: Dec. 31, 2002

(54) ASSAY FOR SCREENING INHIBITORS OF $C_4$ PLANT ENZYMES

(75) Inventors: James Nigel Burnell, Townsville (AU); Lyndon Edwin Llewellyn, Railway Estate (AU)

(73) Assignees: Australian Institute of Marine Science, Townsville (AU); James Cook University of North Queensland, Townsville (AU)

( * ) Notice: Subject to any disclaimer, the term of this patent is extended or adjusted under 35 U.S.C. 154(b) by 0 days.

(21) Appl. No.: 09/673,606

(22) PCT Filed: Apr. 16, 1999

(86) PCT No.: PCT/AU99/00287

§ 371 (c)(1),
(2), (4) Date: Dec. 18, 2000

(87) PCT Pub. No.: WO99/54495

PCT Pub. Date: Oct. 28, 1999

(30) Foreign Application Priority Data

Apr. 17, 1998 (AU) ............................................. PP 3042

(51) Int. Cl.⁷ ............................. C12Q 1/48; C12N 9/04; C12N 9/12; C12N 9/88
(52) U.S. Cl. ....................... 435/15; 435/190; 435/194; 435/232
(58) Field of Search ........................ 435/15, 190, 194, 435/232

(56) References Cited

U.S. PATENT DOCUMENTS 5,429,930 A * 7/1995 Cunningham et al. ........ 435/15
6,068,989 A * 5/2000 Tanaka et al. ................ 422/50

OTHER PUBLICATIONS

Burns and Aberhart, "A General Coupled Spectrophotometric Assay for Decarboxylases," *Analytical Biochemistry*, 171:339–345, 1988.

Jenkins, "Effects of the Phosphoenolpyruvate carboxylate Inhibitor 3,3–Dichloro–2–(Dihydroxyphosphinoylmethyl-)propenoate on Photosynthesis," *Plant Physiol.* 89:1231–1237, 1989.

Mancera et al., "Quantitative Structure–Activity Relationships of Competitive Inhibitors of Phosphoenolypyruvate Carboxylase," *Bioorganic & Medicinal Chemistry* 3(3):217–225, 1995.

McFadden et al., "Potential Inhibitors of Phosphoenolpyruvate Carboxylase. II. Phosphonic Acid Substrate Analogues Derived from Reaction of Trialkyl Phosphites with Halomethacrylates," *Aust. J. Chem.* 42:301–314, 1989.

Ashton et al., "Enzymes of C4 Photosynthesis" (1990) Meth. Plant Biochem., vol. 3, pp. 39–72.*

Lawyer et al., "Use of Pyruvate–Phosphate Dikinase as a Target for Herbicide Design: Analysis of Inhibitor Specificity" (1987) Z. Naturforsch. Sect. C Biosci., 42(6), pp. 834–836.*

Holtum et al., "Activity of Enzymes of Carbon Metabolism During the Induction of Crassulacean Acid Metabolism in Mesembryanthemum crystallinum L." (1982) Planta, vol. 155, pp. 8–16.*

* cited by examiner

*Primary Examiner*—Jon P. Weber
(74) *Attorney, Agent, or Firm*—Seed IP Law Group PLLC

(57) ABSTRACT

An assay to screen potential inhibitors of the $C_4$ acid cycle in plants. The assay involves testing inhibition of $C_4$ enzymes by incubating a mixture that includes pyruvate orthophosphate dikinase, phosphoenolpyruvate carboxylase and malate dehydrogenase and their substrates with a potential inhibitor. Detection of inhibition depends on comparing the resulting levels of NADH or $NAD^+$ in the test mixture to the levels of NADH or $NAD^+$ in a control.

9 Claims, No Drawings

ASSAY FOR SCREENING INHIBITORS OF $C_4$ PLANT ENZYMES

CROSS-REFERENCES TO RELATED APPLICATIONS

This application is a U.S. national stage application of International Application No. PCT/AU99/00287 filed Apr. 16, 1999, which claims priority to Australian Patent Application No. PP 3042 filed Apr. 17, 1998, which applications are incorporated herein by reference in their entireties.

TECHNICAL FIELD

The invention described below relates to an assay procedure for screening potential inhibitors of plant enzymes. In particular, the invention relates to an assay procedure which can be used for the high-throughput screening of potential inhibitors of enzymes of the $C_4$ acid cycle in plants.

BACKGROUND ART

The majority of plants can be divided into $C_3$ and $C_4$ plants, depending on the mechanism the plant uses to incorporate $CO_2$ into organic compounds. In $C_3$ plants, $CO_2$ is initially added onto a five-carbon compound forming an unstable six carbon compound which dissociates into two stable three carbon compounds, hence the $C_3$ name. On the other hand, the first stable compound formed in $C_4$ plants is a four carbon compound. An extra biochemical pathway exists in the leaves of $C_4$ plants which allows them to fix $CO_2$ more efficiently and, under certain environmental conditions, to grow more rapidly than their $C_3$ counterparts. In addition, $C_4$ plants use water and nitrogen more efficiently than $C_3$ plants. Together, these properties enable $C_4$ plants to compete favourably with many of the world's crops, most of which are $C_3$ plants for example, wheat, rice, barley and oats. It follows then that many of the weeds which have an adverse effect on agricultural production throughout the world are $C_4$ plants. Typical examples are nutgrass (*Cyperus rotundus*), couch grass (*Cynodon dactylon*), barnyard grass (*Echinochloa* spp.), Johnson grass (*Sorghum halopense*), and goose grass (*Eleusine indicia*). Nutgrass is a particularly serious global problem being present in more than 100 countries and affecting more than 50 crop species. For efficient agricultural production there is an obvious and pressing need for control of $C_4$ weed species. To date, however, no herbicide specific for $C_4$ weeds has been provided.

Crucial to the $C_4$ acid cycle this being the cycle that fixes $CO_2$ in $C_4$ plants are the following enzymes: pyruvate orthophosphate dikinase (pyruvate,Pi dikinase); phosphoenolpyruvate carboxylase; and, NADP-malate dehydrogenase. The pathway involving these enzymes includes the step which incorporates atmospheric $CO_2$ and creates the products which feed into the sugar-producing Calvin cycle. Interruption of this biochemical pathway should, therefore, adversely affect photosynthesis in $C_4$ plants.

Attempts to develop a $C_4$-specific herbicide have involved designing structural analogues of substrates of the $C_4$ acid cycle enzymes. Those exhibiting inhibitory effects have been further modified to maximise their effect. The only report of a compound which specifically inhibited a $C_4$ enzyme related to 3,3-dichloro-2(dihydroxyphosphinoylmethyl)propenoate which acts on phosphoenolpyruvate carboxylase (see C. L. D. Jenkins et al., *Biochem. Int.* 14, 219–226 [1987]; H. G. McFadden et al., *Aust. J. Chem.* 40, 1619–1629 [1987]; C. L. D. Jenkins, *Plant Physiol.* 89, 1231–1237 [1989]; and, H. G. McFadden et al., *Aust. J. Chem.* 4, 301–314 [1989]). However, the compound was found to have no effect on the growth of $C_4$ plants. At present, none of the compounds known to inhibit enzymes of the $C_4$ acid cycle has herbicidal activity.

Nevertheless, inhibiting the $C_4$ acid cycle to kill $C_4$ plants remains a promising herbicidal strategy. It has been shown that $C_4$ plants transformed by molecular means (antisense technology) to decrease the level of pyruvate, Pi dikinase or phosphoenolpyruvate carboxylase, enzymes specific to the $C_4$ acid cycle, are incapable of surviving unless grown under high $CO_2$ conditions (see J. P. Maroco et al., *Plant Physiol.* 116, 823–832 [1998]). Therefore, it follows that a compound that inhibits either pyruvate, Pi dikinase or phosphoenolpyruvate carboxylase might be an efficient and selective herbicide, thus preventing the deleterious effect of $C_4$ weeds on $C_3$ crops.

Marine organisms are an abundant source of compounds of benefit to humans. Many pharmaceuticals are isolated from plants or are derivatives of compounds first identified in marine organisms. Compounds of marine origin are also known which are enzyme inhibitors. Thus, it is reasonable to assume that because of the diversity of the compounds produced by marine organisms there are likely to be some that are inhibitors of $C_4$ acid cycle enzymes.

In the absence of an indication that an organism produces a compound having desired properties, identification of useful compounds in marine organisms usually entails the screening of extracts from thousands of organisms. However, the known assays for the above three $C_4$ enzymes, which are spectrophotometric assays, are large-volume assays and are not suitable for the screening of large numbers of samples. There is thus a need for an assay which can be used to screen large numbers of samples for potential inhibitors of the $C_4$ acid cycle enzymes.

SUMMARY OF THE INVENTION

The object of the invention is to provide a high-throughput assay which can be used to screen potential inhibitors of enzymes of the $C_4$ acid cycle in plants.

According to a first embodiment of the invention, there is provided an assay for inhibitors of $C_4$ acid cycle enzymes of plants, the assay comprising:

a) testing for inhibition of at least one of pyruvate orthophosphate dikinase, phosphoenolpyruvate carboxylase or malate dehydrogenase by:
 i) including a sample containing the potential inhibitor in a test mixture comprising pyruvate orthophosphate dikinase and substrates thereof, phosphoenolpyruvate carboxylase and the substrate bicarbonate, and malate dehydrogenase and the substrate NADH;
 ii) incubating said test mixture under conditions appropriate for the conversion of pyruvate to malate with oxidation of NADH; and
 iii) detecting inhibition of at least one of said pyruvate orthophosphate dikinase, phosphoenolpyruvate carboxylase or malate dehydrogenase by comparing the level of NADH or NAD$^+$ in said test mixture with the level of NADH or NAD$^+$ in a control mixture incubated under the same conditions as in (a)(ii);

b) testing for inhibition of phosphoenol pyruvate carboxylase or malate dehydrogenase with any sample which contains an inhibitor of at least one of said pyruvate orthophosphate dikinase, phosphoenolpyruvate carboxylase or malate dehydrogenase by:

i) including said sample in a test mixture comprising phosphoenolpyruvate carboxylase and substrates thereof, and malate dehydrogenase and the substrate NADH;

ii) incubating said test mixture under conditions appropriate for the conversion of phosphoenolpyruvate to malate with oxidation of NADH; and iii) detecting inhibition of said phosphoenolpyruvate carboxylase or malate dehydrogenase by comparing the level of NADH or NAD$^+$ in said test mixture with the level of NADH or NAD$^+$ in a control mixture incubated under the same conditions as in (b)(ii);

c) testing for inhibition of malate dehydrogenase with any sample which contains an inhibitor of said phosphoenolpyruvate carboxylase or malate dehydrogenase by:

i) including said sample in a test mixture comprising malate dehydrogenase, oxaloacetate and NADH or including oxaloacetate in said test mixture from a(ii) or b(ii);

ii) incubating said test mixture under conditions appropriate for the conversion of oxaloacetate to malate with oxidation of NADH; and iii) detecting inhibition of said malate dehydrogenase by comparing the level of NADH or NAD$^+$ in said test mixture with the level of NADH or NAD$^+$ in a control mixture incubated under the same conditions as in (c)(ii).

According to a second embodiment of the invention, there is provided an assay for inhibitors of $C_4$ acid cycle enzymes of plants, the assay comprising:

a) testing for inhibition of at least one of pyruvate orthophosphate dikinase, phospho-enolpyruvate carboxylase or malate dehydrogenase by:

i) including a sample containing the potential inhibitor in a test mixture comprising pyruvate orthophosphate dikinase and substrates thereof, phosphoenolpyruvate carboxylase and the substrate bicarbonate, and malate dehydrogenase and the substrate NADH; and ii) incubating said test mixture under conditions appropriate for the conversion of pyruvate to malate with oxidation of NADH;

iii) detecting inhibition of at least one of said pyruvate orthophosphate dikinase, phosphoenolpyruvate carboxylase or malate dehydrogenase by comparing the level of NADH or NAD$^+$ in said test mixture with the level of NADH or NAD$^+$ in a control mixture incubated under the same conditions as in (a)(ii);

b) testing for inhibition of phosphoenolpyruvate carboxylase or malate dehydrogenase with any sample which contains an inhibitor of at least one of said pyruvate orthophosphate dikinase, phosphoenolpyruvate carboxylase or malate dehydrogenase by:

i) including phosphoenolpyruvate in said test mixture from (a)(ii);

ii) incubating said test mixture under said conditions used in step (a)(ii); and iii) detecting inhibition of said phosphoenolpyruvate carboxylase or malate dehydrogenase by comparing the level of NADH or NAD$^+$ in said test mixture with the level of NADH or NAD$^+$ in a control mixture incubated under the same conditions as in (a)(ii);

c) testing for inhibition of malate dehydrogenase with any sample which contains an inhibitor of phosphoenolpyruvate carboxylase or malate dehydrogenase by:

i) including oxaloacetate in said test mixture from (a)(ii) or b(ii) or including said sample in a test mixture comprising malate dehydrogenase, oxaloacetate and NADH;

ii) incubating said test mixture under said conditions used in step (a)(ii); and iii) detecting inhibition of said malate dehydrogenase by comparing the level of NADH or NAD$^+$ in said test mixture with the level of NADH or NAD$^+$ in a control mixture incubated under the same conditions as in (a)(ii).

Other aspects of the invention and the best mode of carrying out the invention will become apparent from a reading of the following detailed description.

DETAILED DESCRIPTION OF THE INVENTION

The following abbreviations are used hereafter:

ATP adenosine triphosphate
AMP adenosine monophosphate
Pi inorganic phosphate
PPi inorganic pyrophosphate
NADH nicotinamide-adenine dinucleotide (reduced form)
NAD$^+$ nicotinamide-adenine dinucleotide (oxidised form)
PPDK pyruvate orthophosphate dikinase (EC 2.7.9.1)
PEP C phosphoenolpyruvate carboxylase (EC 4.1.1.31)
MDH NAD-malate dehydrogenase (EC 1.1.1.37)
HEPES N-[2-hydroxyethyl]piperazine-N'-[2-ethanesulfonic acid]
OAA Oxaloacetate The term "comprising" as used in the above definition of the embodiments and hereafter denotes a mixture or composition which includes at least the specified components but should not be interpreted as meaning that the mixture or composition consists of only those components. Mixtures and compositions can include other ingredients known to those of skill in the art as normal components of mixtures for the assay of enzymes. Examples of these other ingredients include buffers with a suitable $pK_a$ to allow control of the assay mixture within the desired pH range such as HEPES, 2-(N-Morpholino)ethanesulphonic acid (MES), 3-N-Morpholino)propanesulphonic acid (MOPS) or Tris (hydroxymethyl)aminomethane (Tris) but excluding phosphate buffers which will interfere with the reaction; reducing agents such as dithiothreitol or β-mercaptoethanol and salts such as the salts of mono and divalent options. For example PPDK is a divalent cation dependent enzyme and requires the presence of a divalent cation, such as $Mg^{2+}$, $Ca^{2+}$ and $Mn^{2+}$. PEP C is also divalent cation dependent, being dependent on the presence of a divalent metal cation. Other salts, such as ammonium sulphate may be added to improve the performance of the assay.

The present inventors have found that the activities of the $C_4$ plant enzymes PPDK and PEP C can conveniently be assayed in a microtitre plate format using the procedures summarised above thus allowing for the screening of a large number of potential inhibitors of these enzymes or of samples suspected of containing inhibitors. The reactions involved in the assay are as follows:

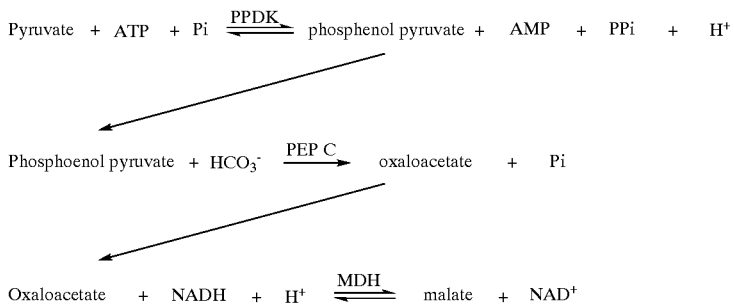

in which the abbreviations set out above have been used. The MDH used for the final reaction in the above sequence is preferably not the $C_4$ plant NADP-dependent enzyme, but is instead the ubiquitous NAD-dependent enzyme. Use of the ubiquitous NAD-dependent enzyme in assays allows elimination of inhibitors that might have a general effect on plants in not being specific for $C_4$ plant enzymes.

As NADH is a substrate for the enzyme catalysing the final reaction in the sequence, the progress of the reaction can be measured via the oxidation of NADH which has a maximal absorbance at 340 nm (range, 300–400 nm). Equally, the reaction can be monitored for the production of $NAD^+$ by the maximal absorbance of $NAD^+$ at approximately 260 nm (range, 230–290 nm). If the latter approach is taken, microtitre plates which have little or no UV absorbing properties are required.

With reference to the assay according to the first embodiment of the invention, step (a) of this assay constitutes a primary screening procedure for compounds active against $C_4$ plant enzymes. Samples identified as containing an active constituent that is, a constituent that reduces the amount of $NAD^+$ formed and thus inhibits at least one of PPDK, PEP C or MDH are then subjected to a secondary screening to determine the enzyme specificity of the inhibitor. The secondary screening is done by assaying individual enzymes in accordance with steps (b) and (c) of the first embodiment and/or by carrying out a physiological assay in accordance with the second embodiment of the invention.

As indicated above, assays can be performed in 96-well microtitre plates. Plates can have wells with round or flat bottoms and can be made of any material that does not have an appreciable absorbance at the wavelength to be measured (260 or 340 nm). The usual volume of a reaction mixture is about 100 μl but this can be adjusted to suit the capacity of the microtitre plate. All that is required is that the absorbance value initially attained is significantly different to the background absorbance of the microtitre plate plus the absorbance of the assay mixture minus NADH or $NAD^+$.

A general description of the method of carrying out a primary screening that is, a screening using the assay according to step (a) of the first embodiment of the invention follows. Typical components of mixtures for this assay and the concentrations of components are set out in Table I

TABLE I

Assay Mixture Components for a Primary Screen

| Reagent | Typical final concentration (mM) | Suitable range (mM) |
|---|---|---|
| Dithiothreitol | 10 | 1–10 |
| $MgSO_4$ | 10 | 2–10 |
| $NaHCO_3$ | 10 | 2–20 |

TABLE I-continued

Assay Mixture Components for a Primary Screen

| Reagent | Typical final concentration (mM) | Suitable range (mM) |
|---|---|---|
| Glucose-6-P | 1 | 0.1–2 |
| $(NH_4)_2SO_4$ | 5 | 0.5–10 |
| $NaH_2PO_4$ | 2.5 | 0.1–5 |
| $NADH_2$ | 0.4 | 0.2–0.5 |
| HEPES pH 8.0 | 50 | 10–200 |
| ATP | 1.6 | 0.5–5 |
| PPDK | as required | as required |
| PEP C | as required | as required |
| MDH | as required | as required |
| Pyruvate | 1 | 0.5–10 |

With regard to the enzymes, assay mixtures typically comprise the following: PPDK, 0.005 units; PEC C; 1 unit; and, MDH, 2 units.

Although a pH of 8.0 is given in Table I above, assays can be performed within a pH range of 6.0 to 9.5.

All mixture components save for at least one of the PPDK substrates are added to wells of a microtitre plate. In addition to test wells to which the test sample is added, positive and negative control wells are also prepared. Positive controls include all assay components save for the test sample. However, an equal volume of test sample solvent (for example, water, methanol, ethanol, DMSO, or mixtures thereof) is added to positive controls. Both test sample and substrate used to initiate the reaction are omitted from the negative control but suitable volumes of the appropriate solvent are added in place of these components. Test wells are typically prepared in duplicate but samples can be tested singly or in greater than two replicates.

After all components have been added to the test and control wells, the plate is usually allowed to equilibrate at room temperature (20–30° C.) for 5 minutes to allow dispersion of test samples and control solvent through the reaction mixtures to give a consistent absorbance reading. This equilibration can be for as little as 1 minute but can also be for up to several hours as the enzymes and other assay components are stable. After equilibration, the absorbance at 340 nm (or 260 nm) is measured using a spectrophotometric plate reader. This measurement is defined as the initial absorbance, $A_0$. The reaction is started by adding, to all but the negative control wells, the substrate pyruvate to the desired final concentration. Alternatively, the test and positive control assay mixtures can be made with pyruvate and without ATP. The reaction is then initiated with ATP.

Plates are incubated at 20 to 30° C. until the reaction is complete as evidenced by a constant reading for the positive controls. This is usually reached after 10 to 60 minutes depending on the amount and activity of the enzymes. The absorbance is then again measured at 340 nm (or 260 nm) to determine the final absorbance, $A_{end}$. To obtain a percent inhibition for an extract being tested, the difference between $A_0$ and $A_{end}$ for the test sample is standardised against the difference between $A_0$ and $A_{end}$ for the positive control.

In the individual enzyme approach to secondary screening of sample extracts having inhibitory activity, the first step is to test active samples against PEP C and MDH. This is step (b) of the first embodiment defined above. Typical components of a PEP C/MDH assay mixture are set out in the following table.

TABLE II

Assay Mixture Components for a PEP C/MDH Assay

| Reagent | Typical final | Suitable range (mM) |
| --- | --- | --- |
| Dithiothreitol | 0 | 1–10 |
| $MgSO_4$ | 10 | 2–10 |
| $NaHCO_3$ | 10 | 2–20 |
| Glucose-6-P | 1 | 0.1–2 |
| $(NH_4)_2SO_4$ | 5 | 0.5–10 |
| $NADH_2$ | 0.4 | 0.2–0.5 |
| HEPES pH 8.0 | 50 | 10–200 |
| PEP C | as required | as required |
| MDH | as required | as required |
| PEP | 5 | 1–10 |

The PEP C/MDH assay is carried out in essentially the same manner as the primary screening assay. If the reaction is not inhibited, specific inhibition of PPDK by active extracts from the primary screen is indicated.

If inhibition is observed in the PEP C and MDH assay, a further assay is conducted in which active extracts are tested against MDH alone. This second step of the secondary screening corresponds to step (c) of the first embodiment. Typical components of an MDH assay mixture are set out in the following table.

TABLE III

Assay Mixture Components for an MDH Assay

| Reagent | Typical final | Suitable range (mM) |
| --- | --- | --- |
| Dithiothreitol | 10 | 1–10 |
| $NADH_2$ | 0.4 | 0.2–0.5 |
| HEPES pH 8.0 | 50 | 10–200 |
| MDH | as required | as required |
| OAA | 1 | 0.5–5 |

If the MDH reaction is not inhibited, the step 1 result can be interpreted as indicating that the inhibitor acts on either PEP C only, or PEP C and PPDK, but not on MDH.

Active extracts identified in the primary screen can also be tested using the physiological assay according to the second embodiment. Inhibition of PPDK is first assessed with the physiological assay using the components listed above in Table I and using essentially the same procedure as for the primary screen. Inhibition of PEP C is then tested by adding the substrate, phosphoenol pyruvate, to the reaction mixture. If an inhibitor is specific for PPDK, no inhibition of PEP C is seen at this stage for the extract containing such an inhibitor. If, however, inhibition is seen, the MDH substrate oxaloacetate is added and the effect of the inhibitor on this enzyme assessed. As with the isolated enzyme approach, normal MDH activity indicates that the inhibitor acts on either PEP C only, or PEP C and PPDK, but not on MDH.

With the assays described above, compounds, or at least extracts containing such compounds, can be identified that are specific inhibitors of the $C_4$ plant enzymes, PPDK and PEP C. The ability to differentiate between inhibitors of these enzymes and inhibitors of MDH allows elimination of those compounds that also act on the more catholic enzyme MDH and thus would not be useful as specific $C_4$ plant herbicides.

It should be noted that while it is not necessary to subject samples which show no inhibition in step a) to further steps b) and c), or to subject samples inactive in step b) to step c), it may be convenient, especially when performing a high throughput assay, to subject all samples to steps a), b) and c) regardless of whether inhibition is seen in steps a) and b). Subjecting all samples to all steps may serve as a useful cross check.

The assays according to the invention can be used to screen for potential inhibitors derived from any source including plants, animals, bacteria, fungi and protozoans. Crude aqueous or organic extracts can be tested, typical organic solvents being methanol, ethanol, dimethylsulfoxide (DMSO) or any combination thereof. Extracts can be acidic or basic provided that any alteration of pH of reaction mixtures on addition of extract does not interfere with the progress of reactions. Compounds able to be tested in the assays include any isolated natural or synthetic product, or any combination of compounds whether produced by combinatorial, purification, or synthetic processes.

The $C_4$ plant enzymes PPDK and PEP C can be prepared by any of the methods known to those of skill in the art. For example, Chapter 3 of *Methods in Plant Biochemistry*, Vol. 3 (Academic Press Limited, London, England, 1990, pp. 39–72), which is by Anthony R. Ashton et al. and is entitled "Enzymes of $C_4$ Photosynthesis", includes summaries of methods for the purification of PPDK and PEP C. The entire content of Chapter 3 of this volume is incorporated herein by cross-reference. MDH is widely available from commercial sources.

Having broadly described the assays according to the invention, the results of application of the assays to the screening of extracts of marine organisms for inhibitors of PPDK and PEP C will now be provided as a non-limiting example of the invention.

EXAMPLE 1

Screening of Extracts of Marine Organisms

Source of Extracts

Extracts were obtained from marine organisms collected via diving, trawling, reef-walking or scissors grab from areas on and off the Australian coastline. The organisms, or portions thereof, were freeze-dried prior to addition of ethanol or methanol as the extracting solvent.

Materials and Methods

Assays were conducted using 96-well microtitre plates obtained from Sarstedt, South Australia. General assay mixture components were obtained from the following: Sigma Chemical Company, St Louis, Mo., USA; Ajax Chemicals, Botany, NSW, Australia; and Boehringer Mannheim Biochemicals, Roche Diagnostics, Basel, Switzerland. PPDK and PEP C were purified from maize and sugar cane as described by Ashton et al. (supra). MDH was obtained from Sigma Chemical Company.

The steps taken in carrying out a primary screen of extracts were as follows:

An assay mixture less initiating substrate and extracts was made up as per the second column of Table I and 100 µl added to wells of a 96-well microtitre plate.

Portions of 10 µl of extract in methanol were added to duplicate wells leaving the last two rows for positive and negative controls. This allowed 40 samples to be tested per plate.

Ten microlitres of methanol was added to the positive and negative control wells.

Ten microlitres of water, the solvent for the initiating substrate, was added to the negative control wells.

Assay mixtures with control solvents and samples were equilibrated at room temperature (26° C.) to allow dispersion of sample and solvent.

An initial absorbance reading ($A_0$) at 340 nm was taken for each well using a Spectra plate reader (Wallac Oy, Turku, Finland).

Ten microlitres of the initiating substrate, pyruvate, in water was added to all wells except the negative control wells. This gave a final pyruvate concentration in the 120 µl assay mixture of 4 mM.

The complete reaction mixtures were incubated for 20 to 30 minutes at room temperature.

After this period, a baseline absorbance was reached in the positive control wells due to exhaustion of the NADH, the baseline absorbance being due to the plastic of the microtitre plate and the residual absorbance of the reaction mixture.

A final absorbance reading ($A_{end}$) was then taken, again at 340 nm.

Percent inhibition in samples was determined by standardising the difference in initial absorbance and final absorbance of the test sample against the difference in initial absorbance and final absorbance of the positive control.

Secondary screening assays were carried out in a similar fashion.

Results

The results presented in Table IV were obtained in a primary screen of 40 test extracts.

TABLE IV

Primary Screening Results

| Extract Number | Average Initial Absorbance | Average Final Absorbance | % inhibition |
|---|---|---|---|
| 2001 | 1.0215 | 0.3185 | 8.2 |
| 2002 | 0.9515 | 0.198 | 1.6 |
| 2003 | 0.9275 | 0.191 | 3.9 |
| 2004 | 1.1185 | 0.4635 | 14.5 |
| 2005 | 1.2945 | 1.2915 | 99.6 |
| 2006 | 0.9675 | 0.2165 | 2.0 |
| 2050 | 0.9765 | 0.4465 | 30.8 |
| 2051 | 0.959 | 0.202 | 1.2 |
| 2052 | 0.9625 | 0.207 | 1.4 |
| 2053 | 1.4055 | 1.509 | 113.5 |
| 2007 | 1.0485 | 0.3565 | 9.7 |
| 2008 | 0.971 | 0.2075 | 0.3 |
| 2009 | 1.0795 | 0.7535 | 57.4 |
| 2011 | 1.029 | 0.992 | 95.2 |
| 2012 | 1.0505 | 0.394 | 14.3 |
| 2013 | 1.0195 | 0.276 | 2.9 |
| 2057 | 0.985 | 0.2465 | 3.6 |
| 2058 | 0.9795 | 0.2315 | 2.3 |
| 2060 | 0.986 | 0.2105 | -1.2 |
| 2061 | 1.014 | 0.227 | -2.7 |
| 2014 | 1.0185 | 0.3545 | 13.3 |
| 2015 | 0.964 | 0.217 | 2.5 |
| 2016 | 1.126 | 0.4515 | 11.9 |
| 2017 | 0.9685 | 0.2145 | 1.6 |
| 2018 | 0.973 | 0.88 | 87.9 |
| 2019 | 1.1195 | 0.4245 | 9.3 |
| 2065 | 0.945 | 0.1985 | 2.5 |
| 2066 | 1.029 | 0.299 | 4.7 |
| 2067 | 0.9595 | 0.191 | -0.3 |
| 2068 | 0.9635 | 0.2175 | 2.6 |

TABLE IV-continued

Primary Screening Results

| Extract Number | Average Initial Absorbance | Average Final Absorbance | % inhibition |
|---|---|---|---|
| 2020 | 0.944 | 0.211 | 4.3 |
| 2022 | 0.9055 | 0.726 | 76.6 |
| 2023 | 0.998 | 0.245 | 1.7 |
| 2025 | 1.0285 | 0.2785 | 2.1 |
| 2028 | 0.9505 | 0.2165 | 4.2 |
| 2029 | 0.9575 | 0.203 | 1.5 |
| 2071 | 1.5085 | 1.746 | 131.0 |
| 2072 | 1.0095 | 0.294 | 6.6 |
| 2076 | 0.9555 | 0.215 | 3.3 |
| 2077 | 0.9415 | 0.1845 | 1.2 |

On the basis of the results obtained in the primary screen, a secondary screen using the isolated enzyme approach was conducted using selected extracts. The results of this screen are presented in Table V.

TABLE V

Secondary Screening Results: PEP C and MDH Activity

| Extract Number | Average Initial Absorbance | Average Final Absorbance | % Inhibition |
|---|---|---|---|
| 2005 | 1.3625 | 0.507 | -1.8 |
| 2011 | 1.09 | 1.0795 | 98.8 |
| 2018 | 1.025 | 0.989 | 95.7 |
| 2053 | 1.3785 | 1.4685 | 110.7 |
| 2071 | 1.6295 | 1.578 | 93.9 |

As the secondary screen indicated that some extracts were active against PPDK and PEP C, or PEP C and/or MDH, certain extracts were tested against MDH alone. The results of these assays are presented in Table VI.

TABLE VI

Secondary Screening Results: MDH Activity

| Extract Number | Average Initial Absorbance | Average Final Absorbance | % Inhibition |
|---|---|---|---|
| 2005 | 1.346 | 0.4895 | -1.4 |
| 2011 | 1.0995 | 0.3745 | 14.2 |
| 2018 | 1.018 | 0.2565 | 9.9 |
| 2053 | 1.307 | 1.4165 | 113 |
| 2071 | 1.815 | 1.7745 | 95.2 |

The results presented in Tables IV to VI show the following: extract 2005 contains a substance that is active against PPDK only; extracts 2011 and 2018 contain substances that are active against either PPDK and PEP C, or PEP C only; and, extracts 2053 and 2071 contain substances that are active against MDH and are thus not specific for $C_4$ enzymes.

A secondary screening was also conducted with selected extracts from Table IV using the physiological assay. Extracts 2053 and 2071 were not tested in this assay as non-specific inhibition was determined in the isolated enzyme assay. No further measurements were needed for extract 2005 after the addition of PEP as this sample had reached its background level at this point.

The results of the physiological assay are presented in the Table VII below.

The results presented in Table VII affirm the earlier results. That is, extract 2005 contains a substance that is active against PPDK only while extracts 2011 and 2018 contain substances which are active against PPDK and PEP C.

TABLE VII

Secondary Screening Results: Physiological Assay

| Extract No. | Initial Absorbance | Final Absorbance (after pyruvate addition) | % Inhibition (PPDK) | Final Absorbance (after PEP addition) | % Inhibition (PEP C) | Final Absorbance (after oxaloacetate addition) | % Inhibition (MDH) |
|---|---|---|---|---|---|---|---|
| 2005 | 1.3845 | 1.433 | 106.1 | 0.6905 | 6.4   | —*     | —*  |
| 2011 | 0.991  | 1.008 | 102.3 | 0.971  | 94.4  | 0.3495 | 2.3 |
| 2018 | 0.9495 | 0.929 | 97.3  | 0.8965 | 95.1  | 0.3    | 6.2 |
| 2053 | —      | —     | —     | —      | —     | —      | —   |
| 2071 | —      | —     | —     | —      | —     | —      | —   |

It will be appreciated that many changes can be made to the assays as exemplified above without departing from the broad ambit and scope of the invention.

What is claimed is:

1. A multiscreening assay for identifying inhibitors of a plant $C_4$ acid cycle enzyme selected from the group consisting of pyruvate orthophosphate dikinase, phosphoenolpyruvate carboxylase and both enzymes, the multi-screening assay comprising at least three screens:
   a) a first screen for testing for inhibition of at least one of pyruvate orthophosphate dikinase, phosphoenolpyruvate carboxylase and malate dehydrogenase by:
      i) including a sample containing the potential inhibitor in a test mixture comprising pyruvate orthophosphate dikinase and substrates thereof, phosphoenolpyruvate carboxylase and the substrate bicarbonate, and malate dehydrogenase and the substrate NADH;
      ii) incubating said test mixture under conditions appropriate for the conversion of pyruvate to malate with oxidation of NADH; and
      iii) detecting inhibition of at least one of said pyruvate orthophosphate dikinase, phosphoenolpyruvate carboxylase and malate dehydrogenase by comparing the level of NADH or $NAD^+$ in said test mixture with the level NADH or $NAD^+$ in a control mixture incubated under the same conditions as in a)(ii);
   b) a second screen for testing for inhibition of phosphoenolpyruvate carboxylase or malate dehydrogenase with any sample which contains an inhibitor from said first screen by:
      i) including said sample in a test mixture containing phosphoenolpyruvate carboxylase and substrates thereof, and malate dehydrogenase and the substrate NADH;
      ii) incubating said test mixture under conditions appropriate for the conversion of phosphoenolpyruvate to malate with oxidation of NADH; and
      iii) detecting inhibition of said phosphoenolpyruvate carboxylase or malate dehydrogenase by comparing the level of NADH or $NAD^+$ in said test mixture with the level of NADH or $NAD^+$ in a control mixture incubated under the same conditions as in b)(ii); and
   c) a third screen for testing for inhibition of malate dehydrogenase with any sample which contains an inhibitor from said second screen by:
      i) including said sample in a test mixture containing malate dehydrogenase, oxaloacetate and NADH or including oxaloacetate in said test mixture from a)(ii) or b)(ii);
      ii) incubating said test mixture under conditions appropriate for the conversion of oxaloacetate to malate with oxidation of NADH; and
      iii) detecting inhibition of said malate dehydrogenase by comparing the level of NADH or $NAD^+$ in said test mixture with the level of NADH or $NAD^+$ in a control mixture incubated under the same conditions as in c)(ii), wherein said inhibitor is identified by detecting inhibition at least in a)(iii) or b)(iii), but substantially no inhibition detected in c)(iii).

2. A multiscreening assay for identifying inhibitors of a plant $C_4$ acid cycle enzyme selected from the group consisting of pyruvate orthophosphate dikinase, phosphoenolpyruvate carboxylase and both enzymes, the multi-screening assay comprising at least three screens:
   a) a first screen for testing for inhibition of at least one of pyruvate orthophosphate dikinase, phosphoenolpyruvate carboxylase and malate dehydrogenase by:
      i) including a sample containing the potential inhibitor in a test mixture comprising pyruvate orthophosphate dikinase and substrates thereof, phosphoenolpyruvate carboxylase and the substrate bicarbonate, and malate dehydrogenase and the substrate NADH;
      ii) incubating said test mixture under conditions appropriate for the conversion of pyruvate to malate with oxidation of NADH; and
      iii) detecting inhibition of at least one of said pyruvate orthophosphate dikinase, phosphoenolpyruvate carboxylase and malate dehydrogenase by comparing the level of NADH or $NAD^+$ in said test mixture with the level of NADH or $NAD^+$ in a control mixture incubated under the same conditions as in a)(ii);
   b) a second screen for testing for inhibition of phosphoenolpyruvate carboxylase or malate dehydrogenase with any sample which contains an inhibitor from said first screen by:
      i) including phosphoenolpyruvate in said test mixture from a)(ii);
      ii) incubating said test mixture under said conditions used in step a)(ii); and
      iii) detecting inhibition of said phosphoenolpyruvate carboxylase or malate dehydrogenase by comparing the level of NADH or $NAD^+$ in said test mixture with the level of NADH or $NAD^+$ in a control mixture incubated under the same conditions as in a)(ii); and
   c) a third screen for testing for inhibition of malate dehydrogenase with any sample which contains an inhibitor from said second screen by:
      i) including oxaloacetate in said test mixture from a)(ii) or b)(ii) or including said sample in a text mixture comprising malate dehydrogenase, oxaloacetate and NADH;
      ii) incubating said test mixture under said conditions used in step a)(ii); and
      iii) detecting inhibition of said malate dehydrogenase by comparing the level of NADH or $NAD^+$ in said test mixture with the level of NADH or $NAD^+$ in a control mixture incubated under the same conditions as in a)(ii), wherein said inhibitor is identified by detecting inhibition at least in a)(iii) or b)(iii), but substantially no inhibition detected in c)(iii).

3. An assay of claim 1 or 2, wherein the level of NADH in one or more of the test mixture is compared to the level of NADH in the corresponding control mixture by comparing the relative absorbances of the mixtures at one or more wavelengths in the range of 300 to 400 nm.

4. An assay of claim 3, wherein the absorbance is measured at a wavelength of 340 mn.

5. An assay of claim 1 or 2, wherein the level of $NAD^+$ in one or more of the test mixture is compared to the level of $NAD^+$ in the corresponding control mixture by comparing the relative absorbances of the mixtures at one or more wavelengths in the range of 230 to 290 mn.

6. An assay of claim 5, wherein the absorbance is measured at a wavelength of about 260 mn.

7. An assay of claim 1 or 2, wherein said multiscreening assay is performed using a microtitre plate.

8. An assay of claim 1 or 2 wherein said first screen is performed with a pH in the range of 6.0 to 9.5.

9. An assay of claim 1 or 2 wherein, in the first screen, one of the substrates for pyruvate orthophosphate dikinase is added last to the test mixture and control as an initiator.

\* \* \* \* \*

UNITED STATES PATENT AND TRADEMARK OFFICE
CERTIFICATE OF CORRECTION

PATENT NO.   : 6,500,632 B1
DATED        : December 31, 2002
INVENTOR(S)  : James Nigel Burnell and Lyndon Edwin Llewellyn It is certified that error appears in the above-identified patent and that said Letters Patent is hereby corrected as shown below:

Column 13,
Line 2, "at a wavelength of 340 mn." should read -- at a wavelength of 340 nm. --
Line 7, "in the range of 230 to 290 mn." should read -- in the range of 230 to 290 nm. --
Line 9, "wavelength of about 260 mn." should read -- wavelength of about 260 nm. --

Signed and Sealed this

Twenty-second Day of April, 2003

JAMES E. ROGAN
*Director of the United States Patent and Trademark Office*